(12) United States Patent
Kim et al.

(10) Patent No.: US 9,521,980 B2
(45) Date of Patent: Dec. 20, 2016

(54) METHOD FOR REGISTERING MEDICAL IMAGES, APPARATUS PERFORMING THE METHOD, AND COMPUTER READABLE MEDIA INCLUDING THE METHOD

(71) Applicant: SAMSUNG ELECTRONICS CO., LTD., Suwon-si (KR)

(72) Inventors: Jungbae Kim, Seoul (KR); Youngkyoo Hwang, Seoul (KR); Youngtaek Oh, Seoul (KR); Wonchul Bang, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 39 days.

(21) Appl. No.: 14/547,965

(22) Filed: Nov. 19, 2014

(65) Prior Publication Data

US 2015/0332461 A1 Nov. 19, 2015

(30) Foreign Application Priority Data

May 16, 2014 (KR) .................. 10-2014-0059302

(51) Int. Cl.
G06K 9/00 (2006.01)
A61B 6/03 (2006.01)
G06T 7/00 (2006.01)
A61B 6/00 (2006.01)
A61B 8/00 (2006.01)
(Continued)

(52) U.S. Cl.
CPC ............ *A61B 6/032* (2013.01); *A61B 6/4417* (2013.01); *A61B 6/5247* (2013.01); *A61B 8/4416* (2013.01); *A61B 8/5261* (2013.01);
*G06T 7/0024* (2013.01); *G06T 7/0028* (2013.01); *A61B 5/055* (2013.01); *A61B 6/037* (2013.01); *G06T 2207/10004* (2013.01); *G06T 2207/10072* (2013.01); *G06T 2207/10081* (2013.01); *G06T 2207/10092* (2013.01);
(Continued)

(58) Field of Classification Search
CPC combination set(s) only.
See application file for complete search history.

(56) References Cited

U.S. PATENT DOCUMENTS 5,951,475 A * 9/1999 Gueziec ............... G06T 3/0068
128/922
7,327,872 B2 * 2/2008 Vaillant ................. A61B 6/032
382/128
(Continued)

FOREIGN PATENT DOCUMENTS

JP 2008-86400 A 4/2008
JP 2009-291618 A 12/2009
(Continued)

*Primary Examiner* — Anand Bhatnagar
(74) *Attorney, Agent, or Firm* — Sughrue Mion, PLLC

(57) ABSTRACT

A medical image registration method includes performing a first registration by registering first medical images, including a registration image and a display image, the display image being an image to be displayed, performing a second registration by registering a second medical image having a different modality than a modality of the first medical images, with the registration image, and extracting a cross-section of one of the first medical images, corresponding to a cross-section of the second medical image, from the display image, according to the first registration and the second registration.

18 Claims, 3 Drawing Sheets

(51) Int. Cl.
  *A61B 8/08* (2006.01)
  *A61B 5/055* (2006.01)
(52) U.S. Cl.
  CPC .............. *G06T 2207/10116* (2013.01); *G06T 2207/10132* (2013.01); *G06T 2207/30056* (2013.01)

(56) References Cited

U.S. PATENT DOCUMENTS

| | | | |
|---|---|---|---|
| 7,499,743 B2* | 3/2009 | Vass | G06T 7/0028 600/407 |
| 8,929,624 B2* | 1/2015 | Knoplioch | A61B 19/56 345/419 |
| 2005/0197568 A1* | 9/2005 | Vass | G06T 7/0028 600/426 |
| 2009/0054772 A1* | 2/2009 | Lin | A61N 7/02 600/439 |
| 2009/0080749 A1* | 3/2009 | Visser | G06T 5/50 382/131 |
| 2010/0268085 A1* | 10/2010 | Kruecker | A61B 8/0833 600/443 |
| 2011/0028844 A1 | 2/2011 | Hyun et al. | |
| 2012/0253170 A1* | 10/2012 | Kim | A61B 19/50 600/410 |
| 2013/0057547 A1* | 3/2013 | Hwang | G06T 17/00 345/420 |
| 2014/0321726 A1* | 10/2014 | Shin | A61B 8/5261 382/131 |

FOREIGN PATENT DOCUMENTS

| | | |
|---|---|---|
| JP | 2013-106780 A | 6/2013 |
| KR | 10-1121396 B1 | 3/2012 |

\* cited by examiner

METHOD FOR REGISTERING MEDICAL IMAGES, APPARATUS PERFORMING THE METHOD, AND COMPUTER READABLE MEDIA INCLUDING THE METHOD

CROSS-REFERENCE TO RELATED APPLICATION

This application claims priority to Korean Patent Application No. 10-2014-0059302, filed on May 16, 2014, in the Korean Intellectual Property Office, the disclosure of which is incorporated herein in its entirety by reference.

BACKGROUND

1. Field

The exemplary embodiments relate to a method of matching medical images having different modalities, an apparatus performing the method, and a computer readable recording medium including the method.

2. Description of the Related Art

With recent developments in medical technology, high resolution medical images may be obtained. As a medical device may be finely manipulated, a method of forming a small puncture hole in the skin, directly inserting a catheter or a medical needle into a blood vessel or a desired body part, and providing treatment while observing the interior of the body by using a medical imaging device, without needing to cut and expose the desired body part, has been developed. The method is referred to as a "treatment method using an image" or an "interventional imaging method".

A practitioner recognizes a location of an organ or a lesion by using an image. In addition, since a patient breathes or moves, the practitioner has to recognize a change in a position of the target area according to the breathing or movement. Accordingly, the practitioner has to provide treatment by accurately and quickly recognizing the breathing or the movement based on an image in real time. In this case, however, it is not easy to recognize with the naked eye a shape of the organ or the lesion in an ultrasound image that may be obtained in real time.

A magnetic resonance (MR) or computed tomography (CT) image, unlike the ultrasound image, enables the practitioner to clearly identify the organ or the lesion. However, since the MR or CT image may not be obtained in real time during medical treatment, the MR or CT image may fail to reflect the patient's breathing or movement that occurs during the medical treatment.

SUMMARY

Provided are methods of matching medical images having different modalities, apparatuses performing the methods, and computer readable recording media including the methods.

Additional aspects will be set forth in part in the description which follows and, in part, will be apparent from the description, or may be learned by practice of the presented exemplary embodiments.

According to an aspect of an exemplary embodiment, there is provided a medical image registration method including performing a first registration by registering first medical images, including a registration image and a display image, the display image being an image to be displayed; performing a second registration by registering a second medical image, having a different modality than a modality of the first medical images, with the registration image; and extracting a cross-section of one of the first medical images corresponding to a cross-section of the second medical image from the display image, according to the first registration and the second registration.

The cross-section of the one first medical image and the cross-section of the second medical image may correspond to a same view of an object.

The registration image and the display image may be images obtained by imaging an object at different points of time.

A sub-object included in the registration image may have a different degree of clarity from a same sub-object included in the display image.

A first sub-object may be clearer than a second sub-object in the registration image, and the second sub-object may be clearer than the first sub-object in the display image.

The medical image registration method may further include calculating a first conversion relationship which is a conversion relationship between the registration image and the display image, via the first registration.

The medical image registration method may further include calculating a second conversion relationship which is a conversion relationship between the second medical image and the registration image, via the second registration.

The extracting the cross-section of one of the first medical images may include converting coordinate information about the cross-section of the second medical image into coordinate information in the registration image according to the second registration; converting the coordinate information in the registration image into coordinate information in the display image according to the first registration; and extracting the cross-section of the one first medical image having the coordinate information in the display image, from the display image.

The medical image registration method may further include displaying the cross-section of the one first medical image and the cross-section of the second medical image together.

The one first medical image may be a pre-captured medical image, and the second medical image may be captured in real time.

The first medical image may be at least one of a magnetic resonance (MR) image, a computed tomography (CT) image, a position emission tomography (PET) image, a single-photon emission computed tomography (SPECT) image, and an X-ray image, and the second medical image may be an ultrasound image.

According to another aspect of an exemplary embodiment, there is provided a medical imaging apparatus including a first registrator configured to perform a first registration by registering first medical images, including a registration image and a display image, the display image being an image to be displayed; a second registrator configured to perform a second registration by registering a second medical image, having a different modality than a modality of the first medical images, with the registration image; and an extractor configured to extract a cross-section of one of the first medical images corresponding to a cross-section of the second medical image from the display image, according to the first registration and the second registration.

The cross-section of the one first medical image and the cross-section of the second medical image may correspond to a same view of an object.

The registration image and the display image may be images obtained by imaging an object at different points of time.

A sub-object included in the registration image may have a different degree of clarity from a same sub-object included in the display image.

A first sub-object may be clearer than a second sub-object in the registration image, and the second sub-object may be clearer than the first sub-object in the display image.

The extractor may be configured to convert coordinate information about the cross-section of the first medical image into coordinate information in the registration image according to the second registration, convert the coordinate information in the registration image into coordinate information in the display image according to the first registration, and extract the cross-section of the second medical image having the coordinate information in the display image, from the display image.

The medical imaging apparatus may further include a display configured to display the cross-section of the one first medical image and the cross-section of the second medical image together.

The one first medical image may be a pre-captured medical image, and the second medical image may be captured in real time.

BRIEF DESCRIPTION OF THE DRAWINGS

The above and/or other aspects will become more apparent by describing certain exemplary embodiments, taken in conjunction with the accompanying drawings, in which.

DETAILED DESCRIPTION

Figure 1:
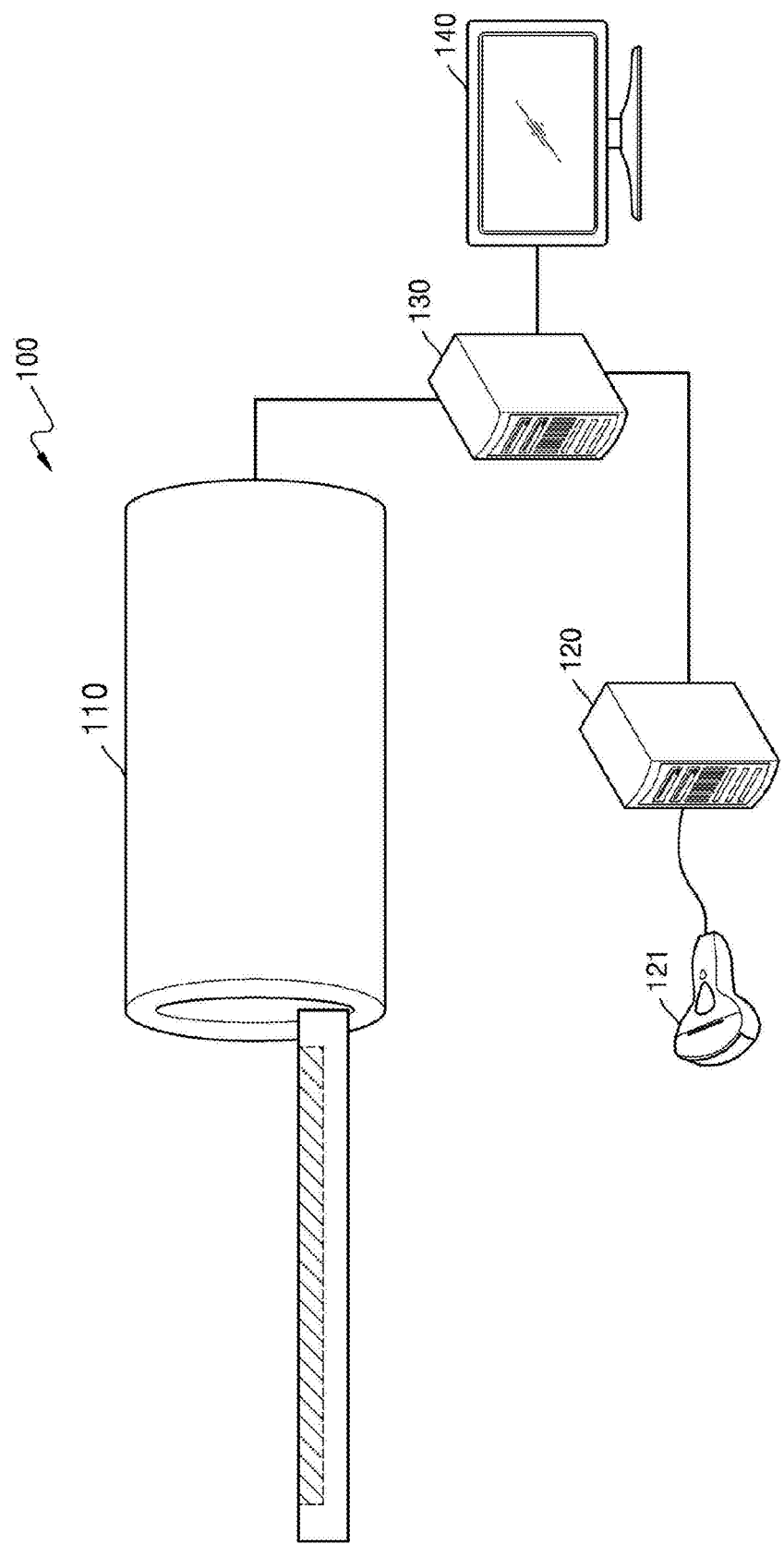
FIG. 1 is a schematic diagram of a system according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, certain exemplary embodiments are merely described below, by referring to the figures, to explain aspects of the exemplary embodiments.

The term "object" used herein may include a human, an animal, or a body part of a human or animal. For example, the object may include the liver, the heart, the womb, the brain, a breast, the abdomen, or a blood vessel. Also, the term "user" used herein may refer to, but is not limited to, a medical expert such as a doctor, a nurse, a clinical pathologist, a medical image expert, or an engineer who repairs a medical device.

FIG. 1 is a schematic diagram of a system 100 according to an exemplary embodiment. Referring to FIG. 1, the system 100 includes a first medical apparatus 110, a second medical apparatus 120, a registration apparatus 130, and a display apparatus 140.

The first medical apparatus 110 and the second medical apparatus 120 respectively generate a first medical image and a second medical image and respectively provide the first medical image and the second medical image to the registration apparatus 130. The first medical image and the second medical image have different modalities. In other words, the first medical image and the second medical image may have different generation methods and principles. The registration apparatus 130 receives the first medical image and the second medical image, and registers the first medical image and the second medical image having different modalities. The first medical image and second medical image registered by the registration apparatus 140 may be displayed on the display apparatus 150.

The first medical apparatus 110 provides the first medical image of a volume of interest (VOI) of an object in non-real time. Considering the non-real time characteristics of the first medical apparatus 110, the first medical image may be previously captured before medical treatment.

For example, the first medical apparatus 110 may be any one of a computed tomography (CT) apparatus, a magnetic resonance (MR) imaging apparatus, an X-ray imaging apparatus, a single-photon emission computed tomography (SPECT) apparatus, and a position emission tomography (PET) apparatus. For convenience of explanation, the following will be described on the assumption that the first medical image is an MR or CT image, but the present exemplary embodiment is not limited thereto.

In the CT image or MR image generated by the first medical apparatus 110, a location of an organ or a location of a lesion may be clearly distinguished. However, when the patient breaths or moves, the organ may be deformed or displaced. In this case, the CT or MR image might not reflect in real time the deformation or displacement of the organ as the patient breathes or moves.

The reason why the first medical apparatus 110 might not output an image in real time is that in the case of the CT image, since the CT image is captured by using radiation, this creates a risk that the patient and a practitioner may be exposed to the radiation if the CT image is captured for a long time, and, thus, short time image-capturing is recommended. Further, in the case of the MR image, it takes a long time to capture the MR image. In general, the CT image is captured when the patient temporarily stops breathing, for example, inhales deeply.

The second medical apparatus 120 provides in real time the second medical image of the VOI of the object. For example, when an organ is deformed or displaced due to the object's physical activity, the second medical image is changed in real time. However, all organs and lesions may not be clearly observed in the second medical image and it is difficult to recognize the deformation and the displacement of the organ by using only the second medical image.

In an exemplary embodiment, the second medical apparatus 120 may be an ultrasonography machine that generates an image in real time during interventional medical treatment performed on a patient. However, an exemplary embodiment is not limited thereto, and the second medical apparatus 120 may be any of other medical apparatuses such as an optical coherence tomography (OCT) apparatus that provides an image in real time.

When the second medical apparatus 120 is an ultrasonography machine, the second medical apparatus 120 generates an ultrasound image by emitting ultrasound to the object by using a probe 121 and detecting reflected ultrasound. The probe 121 may generally include a piezoelectric transducer. However, the present exemplary embodiment is not limited thereto. For example, the probe 121 may be a capacitive micromachined ultrasonic transducer (cMUT) that converts ultrasound into an electrical signal or vice versa due to a change in capacitance, a magnetic micromachined ultrasonic transducer (mMUT) that converts ultrasound into an electrical signal or vice versa due to a change in a magnetic field, or an optical ultrasonic detector that converts ultrasound into an electrical signal or vice versa due to a change in optical characteristics.

When ultrasound is applied at several tens to hundreds of MHz from the probe 121 to a specific portion in the patient's body, the ultrasound is partially reflected from layers between various different tissues. The ultrasound is reflected from sub-objects having different densities in the patient's body, for example, blood cells in blood plasma or small structures in organs.

The reflected ultrasound vibrates a transducer of the probe 121, and the transducer outputs electrical pulses according to the vibration. The electrical pulses are converted into an image. When sub-objects have different ultrasound reflection characteristics, the sub-objects may be displayed with different brightness values in an ultrasound image in a B mode.

A medical image generated by the first medical apparatus 110 or the second medical apparatus 120 may be a three-dimensional (3D) image that is generated by stacking two-dimensional (2D) cross-sections. For example, the first medical apparatus 110 captures a plurality of cross-sections by changing a location or an orientation of the cross-section. When the cross-sections are stacked, 3D volume image data three-dimensionally representing a specific portion of the patient's body may be generated. A method of generating 3D volume image data by stacking cross-sections is referred to as multiplanar reconstruction (MPR). Similarly, the second medical apparatus 120 may generate 3D volume image data by hand-sweeping or wobbling the probe 121 that is a 2D array probe.

The following will be described on the assumption that the first medical image and the second medical image are 3D images. The first medical image may be an image having a contrast which is enhanced in order to increase the brightness of the patient's organ of interest.

Medical images that can be obtained by the second medical apparatus 120, for example, ultrasound images, may be obtained in real time, but may include a lot of noise. Thus, it may be difficult to identify the contours of organs, internal structures, or lesions from the ultrasound images. The reason for this difficulty is that, since a lesion and its peripheral tissue in the ultrasound image have similar ultrasound characteristics, a contrast appearing at the boundary between the lesion and its peripheral tissue, namely, an edge contrast of a sub-object, is relatively low in the ultrasound image. In addition, the ultrasound image has noise and artifacts due to interference and scattering of ultrasound. In other words, since ultrasound medical images have a low signal to noise ratio (SNR) and a low edge contrast of a sub-object, although the ultrasound medical images may be quickly acquired compared to MR or CT images, it may be difficult to accurately identify organs and lesions from the ultrasound images in contrast with MR or CT images.

The registration apparatus 130 registers the first medical image that is obtained from the first medical apparatus 110 and the second medical image that is obtained from the second medical apparatus 120. The registration of the first and second medical images may include matching a coordinate system used by the first medical apparatus 110 and a coordinate system used by the second medical apparatus 120. For example, the first medical apparatus 110 and the second medical apparatus 120 may use a coordinate system based on the Digital Imaging and Communication in Medicine (DICOM) standard.

According to an exemplary embodiment, the registration apparatus 130 may register a first medical image of a liver region and a second medical image thereof by using information about an inferior vena cava (IVC) and a diaphragm that are clearly shown in both the first medical image and the second medical image. Accordingly, even when information about a liver, which is the patient's organ of interest, is lost from the second medical image, the first and second medical images of the liver region may be registered using the IVC and the diaphragm.

The liver, the diaphragm, and the IVC are only examples, and exemplary embodiments are not limited to these examples. For example, when the organ of interest is a liver, at least one selected from a kidney, a gall bladder, a portal vein, a hepatic vein, and an IVC that are disposed adjacent to the liver may be used. When the organ of interest is a kidney, at least one selected from the IVC, the liver, the gall bladder, a spleen, and a renal vein that are disposed adjacent to the kidney may be used. When the organ of interest is a thyroid, at least one selected from a carotid and a jugular vein that are disposed adjacent to the thyroid may be used. When the organ of interest is a pancreas, at least one selected from the IVC, a splenic vein, a splenic artery, and the spleen that are disposed adjacent to the pancreas may be used.

In an exemplary embodiment, a registered image may be a fusion image obtained by fusing the first medical image and the second medical image. In another exemplary embodiment, the registered image may be an image obtained by arranging the first medical image and the second medical image in parallel at the same observation view. The registered image is displayed on the display apparatus 140.

Although the second medical apparatus 120, the registration apparatus 130, and the display apparatus 140 are independent apparatuses in FIG. 1, it will be understood that the second medical apparatus 120, the registration apparatus 130, and the display apparatus 140 may be integrated into one apparatus.

Even in the first medical image, a degree of clarity of a sub-object may vary according to the time when the first medical image is captured. For example, when the first medical image is an MR image of a liver, sub-objects that are clearly shown in the MR image may vary according to an arterial-dominant phase, a portal-venous phase, or a delayed phase.

Figure 2A:
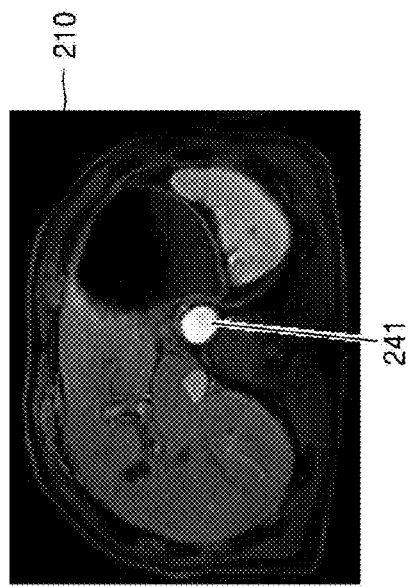
FIGS. 2A, 2B, and 2C show magnetic resonance (MR) images of a liver that are captured at different points of time, according to an exemplary embodiment.
Figure 2C:
Figure 2B:
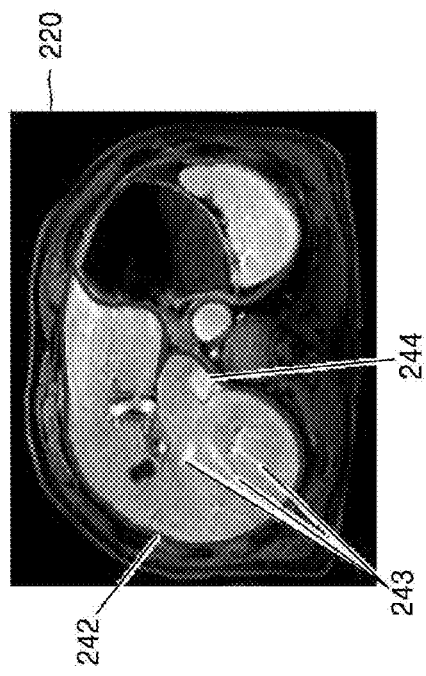

FIGS. 2A, 2B, and 2C show MR images obtained by imaging a liver at different points of time, according to an exemplary embodiment. FIG. 2A shows an arterial-dominant phase image 210, FIG. 2B shows a portal-venous phase image 220, and FIG. 2C shows a delayed phase image 230. As shown in FIGS. 2A, 2B, and 2C, an abdominal aorta (AA) 241 from among sub-objects of the liver is clearly shown in the arterial-dominant phase image 210, a liver surface 242, vessels 243, and an IVC 244 is clearly shown in the portal-venous phase image 220, and tumors 245 are clearly shown on the delayed phase image 230.

Thus, an ultrasound image and an MR image may be easily registered by selecting the AA 241 or the liver surface 242, which are sub-objects commonly clearly shown on the ultrasound image and either the arterial-dominant phase image 210 or the portal-venous phase image 220, as a feature and registering the selected feature of the ultrasound image and that of the MR image. However, displaying an MR image clearly showing a tumor is useful to a user during diagnosis, and thus the delayed phase image 230 may be displayed. Accordingly, when medical images having different modalities are registered, a registration image and a display image may be different.

Figure 3:
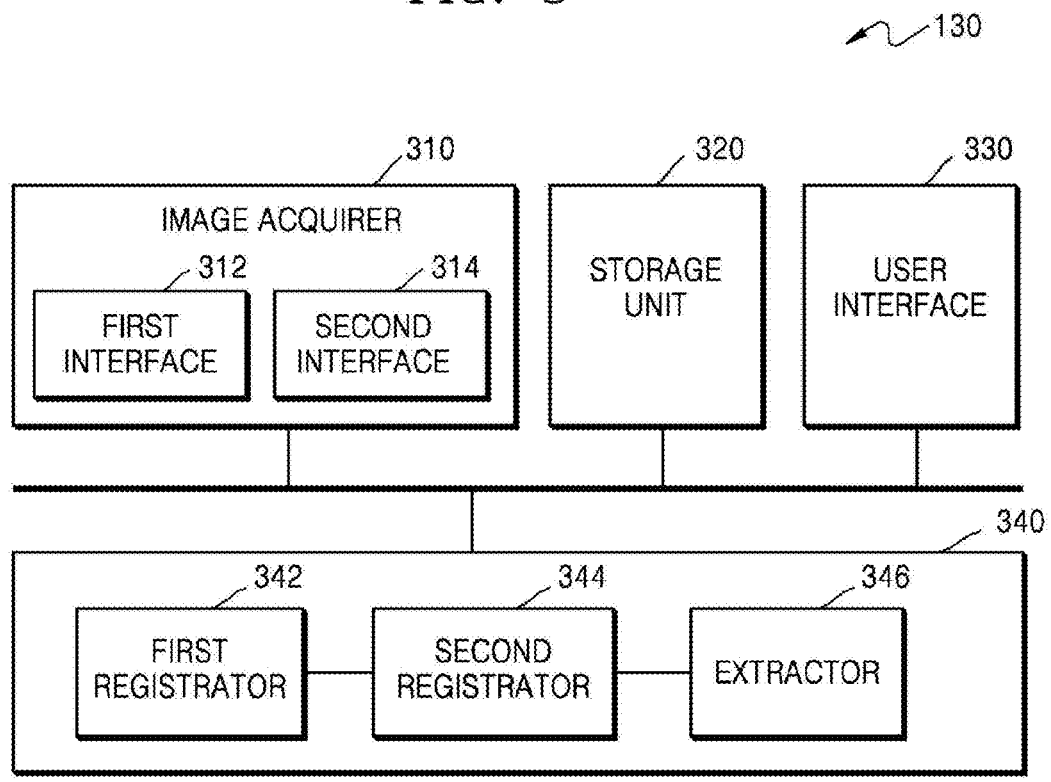
FIG. 3 is a block diagram of a registration apparatus included in the system of FIG. 1.

FIG. 3 is a block diagram illustrating the registration apparatus 130 of FIG. 1, according to an exemplary embodiment. Referring to FIG. 3, the registration apparatus 130 may include an image acquisition unit 310 (e.g., image acquirer), a storage unit 320, a user interface 330, and an image processing unit 340 (e.g., image processor). However, the elements illustrated in FIG. 3 may not be essential elements, and the registration apparatus 130 may further include general-purpose elements other than the elements illustrated in FIG. 3.

The image acquisition unit 310 may respectively acquire a first medical image and a second medical image from the first medical apparatus 110 and the second medical apparatus 120. The image acquisition unit 310 includes first and second interfaces 312 and 314 for respectively obtaining the first medical image and the second medical image from the first medical apparatus 110 and the second medical apparatus 120. The first interface 312 and the second interface 314 are interfaces that are directly or indirectly connected to the first medical apparatus 110 and the second medical apparatus 120 respectively.

The first interface 312 may be directly connected to the first medical apparatus 110 to obtain the first medical image that is previously generated by the first medical apparatus 110 before medical treatment. Alternatively, the first interface 312 may be omitted when the first medical image is obtained via another external storage medium (such as a universal serial bus (USB), a compact disc (CD), or a digital versatile disc (DVD)) or via a network interface (e.g., local area network (LAN) or the Internet). The image acquisition unit 310 may store the obtained first medical image in the storage unit 320. The first medical image may be a plurality of images captured at different points of time. For example, when the first medical image is an MR image of a liver, the first medical image may include at least two selected from an arterial-dominant phase image, a portal-venous phase image, and a delayed phase image. The second interface 314 may acquire the second medical image captured by the second medical apparatus 120 and acquire the cross-section of the second medical image in real time.

The user interface 330 receives an input for manipulating the registration apparatus 130 from the user, and outputs the first medical image, the second medical image, or a registered medical image obtained by the registration apparatus 130. The user interface 330 may include buttons, a keypad, a switch, dials, or a touch interface by which the user may directly manipulate the registration apparatus 130. The user interface 330 may include a display unit for displaying an image, and may be a touch screen. In another exemplary embodiment, the user interface 330 may include an input/output (I/O) port for connecting human interface devices (HIDs). The user interface 330 may include an I/O port for inputting and/or outputting an image.

The image processing unit 340 may register the first medical image and the second medical image and output a registered image to the user interface 330. The image processing unit 340 may include a first registration unit 342 (e.g., first registrator), a second registration unit 344 (e.g., second registrator), and an extraction unit 346 (e.g., extractor). The first registration unit 342 registers a plurality of first medical images, that is, performs first registration. When registering the plurality of first medical images, the first registration unit 342 extracts a common feature from the plurality of first medical images. For example, when the plurality of first medical images are MR images of a liver, the first registration unit 342 may select a liver surface as the common feature and match liver surfaces in the MR images to thereby register the MR images of the liver. The plurality of first medical images may have the same coordinate system, and may have fine misalignments therebetween. When registering the plurality of first medical images, the first registration unit 342 may calculate conversion relationships between the first medical images.

The first registration unit 342 may register the plurality of first medical images by matching the first medical images in a one-to-one correspondence, or may register the plurality of first medical images by fusing the plurality of first medical images to generate a single fusion image. A registered image obtained by the first registration unit 342 may be stored in the storage unit 320. For convenience of explanation, the first registration unit 342 will be described as matching the first medical images in a one-to-one correspondence. However, the present exemplary embodiment is not limited thereto. For example, the first registration unit 342 may generate an arterial-dominant phase image, a portal-venous phase image, and a delayed phase image of a liver as a single image.

Some of the plurality of first medical images may be registration images that are used for registration with the second medical image, and the others may be display images that are used for being displayed with the cross-section of the second medical image. Each of the registration images and the display images may include a plurality of sub-objects, for example, an AA, an IVC, a surface, and a tumor. At least some of the sub-objects included in each of the registration images and the display images may be different in terms of degree of clarity. For example, an AA may be clearly shown in the arterial-dominant phase image, a liver surface, a vessel, and an IVC may be clearly shown in the portal-venous phase image, and tumors may be clearly shown in the delayed phase image. Since the liver surface, the AA, or the vessel is also clearly shown in an ultrasound image, the arterial-dominant phase image and the portal-venous phase image may be used as the registration images. Since a user may desire to identify the location of a tumor, which is a sub-object, during a medical treatment, the delayed phase image may be used as a display image.

The second registration unit 344 may register a registration image and the second medical image, that is, perform second registration. The second registration unit 344 may register the registration image and the second medical image by selecting a common feature from each of the registration images and the second medical image and matching the common features. For example, the second registration unit 344 extracts a vessel or a liver surface from the arterial-dominant phase image or the portal-venous phase image from among the MR images of the liver. The second registration unit 344 also extracts a vessel or a liver surface from an ultrasound image of the liver. Then, the second registration unit 344 may match the vessel or liver surface of the MR image with the vessel or liver surface of the ultrasound image to thereby register the registration image and the ultrasound image. The second registration unit 344 may calculate a conversion relationship between the registration image and the second medical image via the registration of the registration image and the second medical image.

The second medical apparatus 120 may apply the cross-section of the second medical image to the registration apparatus 130 in real time. When coordinate information about the cross-section of the second medical image changes as the probe 121 rotates or moves, the registration apparatus 130 may receive a cross-section of the second medical image having changed coordinate information from the second medical apparatus 120.

Then, the extraction unit 346 may extract a cross-section of the first medical image corresponding to the cross-section of the second medical image from the display image, by using the first registration and the second registration. In detail, the extraction unit 346 may convert the coordinate information about the cross-section of the second medical image into coordinate information in the registration image by using the second registration, convert the coordinate information in the registration image into coordinate information in the display image, and extract a cross-section having the coordinate information in the display image from the display image. The cross-section of the first medical image and the cross-section of the second medical image may correspond to the same view of an object. For example, the extraction unit 346 converts coordinate information about the cross-section of the ultrasound image into coordinate information in the arterial-dominant phase image which is a registration image, and converts the coordinate information in the arterial-dominant phase image into coordinate information in the delayed phase image which is a display image. The extraction unit 346 may extract a cross-section having the coordinate information in the delayed phase image from the delayed phase image.

The cross-section of the first medical image and the cross-section of the second medical image may be applied to the display apparatus 140 or the user interface 330 and may be displayed together thereon. The cross-section of the first medical image and the cross-section of the second medical image may be displayed on different regions or may be fused into a single image and then displayed.

Figure 4:
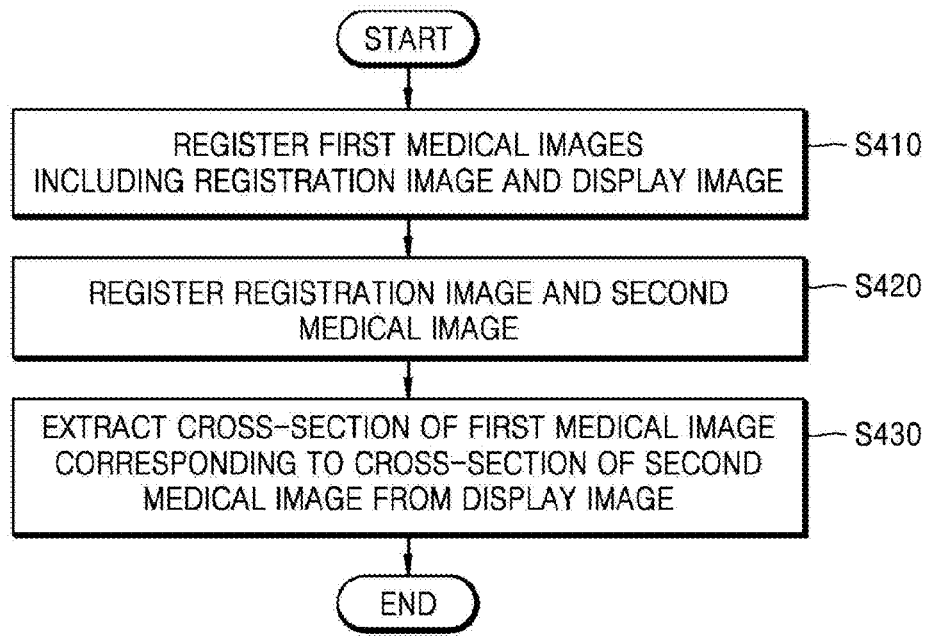
FIG. 4 is a flowchart of a method of registering medical images, according to an exemplary embodiment.

FIG. 4 is a flowchart of a method of registering medical images, according to an exemplary embodiment. Referring to FIG. 4, the first registration unit 342 of the registration apparatus 130 registers a plurality of first medical images including a registration image and a display image (hereinafter, referred to as first registration), in operation S410. The registration apparatus 130 receives the plurality of first medical images from the first medical apparatus 110. The plurality of first medical images may be 3D images. The registration image and the display image may be images captured at different points of time, and at least some of the sub-objects included in each of the registration image and the display image may be different in terms of degree of clarity. For example, a first sub-object may be clearer than a second sub-object in the registration image, and the second sub-object may be clearer than the first sub-object in the display image.

The first registration unit 342 may register the registration image and the display image by selecting a common feature from each of the registration image and the display image and matching the selected common features. The registration image and the display image may be registered in various other ways.

By registering the plurality of first medical images, the first registration unit 342 may calculate a first conversion relationship $T_1$ between a registration image $X_{MR1}$ and a display image $X_{MR2}$, which is a conversion relationship between the registration image and the display image, as shown in Equation 1 below. The first registration unit 342 may store the plurality of first medical images and the first conversion relationship $T_1$ in the storage unit 320.

$$T_1 = x_{MR2} x_{MR1}^{-1} \quad \text{[Equation 1]}$$

In operation S420, the second registration unit 344 may register the registration image and a second medical image (hereinafter, referred to as second registration). The registration apparatus 130 may receive the second medical image from the second medical apparatus 120, and the second registration unit 344 may download the registration image from the storage unit 320. The second medical image has a different modality than the registration image, namely, a first medical image. The second registration unit 344 may register the registration image and the second medical image by selecting a common feature from each of the registration image and the second medical image and matching the selected common features. The registration image and the second medical image may be registered in other various ways.

By registering the registration image and the second medical image, the second registration unit 344 may calculate a second conversion relationship $T_2$ between the registration image $X_{MR1}$ and a second medical image $X_{UR}$, which is a conversion relationship between the registration image and the second medical image, as in Equation 2 below. The second conversion relationship $T_2$ calculated by the second registration unit 344 may be stored in the storage unit 320.

$$T_2 = x_{MR1} x_{UR}^{-1} \quad \text{[Equation 2]}$$

In operation S430, the extraction unit 346 may extract a cross-section of the first medical image corresponding to the cross-section of the second medical image from the display image, by using the first registration and the second registration. The image acquisition unit 310 may acquire the cross-section of the second medical image and the coordinate information about the cross-section of the second medical image from the second medical apparatus 120. The coordinate information may include at least one selected from a direction and a position of the cross-section of the second medical image. The extracted cross-section of the second medical image and the extracted coordinate information about the cross-section of the second medical image are applied to the extraction unit 346. The extraction unit 346 converts coordinate information $X_{UR(t)}$ about the cross-section of the second medical image into coordinate information $X_{MR1(t)}$ in the registration image by using the second conversion relationship $T_2$ calculated during the second registration, as shown in Equation 3:

$$x_{MR1(t)} = T_2 x_{UR(t)} \quad \text{[Equation 3]}$$

The extraction unit 346 also converts the coordinate information $X_{MR1(t)}$ in the registration image into coordinate information $X_{MR2(t)}$ in the display image by using the first conversion relationship $T_1$ calculated during the first registration, as shown in Equation 4:

$$x_{MR2(t)} = T_1 x_{MR1(t)} \quad \text{[Equation 4]}$$

The extraction unit 346 may extract a cross-section having the coordinate information $X_{MR2(t)}$ in the display image from the display image. The cross-section of the first medical image and the cross-section of the second medical image may correspond to the same view of the object.

The cross-section of the first medical image and the cross-section of the second medical image may be displayed via the user interface 330 or the display apparatus 140. The cross-section of the first medical image and the cross-section of the second medical image may be displayed on different regions on a single screen or may be displayed to overlap with each other in a single region.

The method of registering medical images can be written as computer programs and can be implemented in general-use digital computers that execute the programs using a computer readable recording medium. A structure of the data used in the above-described exemplary embodiment may be recorded in a computer readable recording medium via several units. Examples of the computer readable recording medium include magnetic storage media (e.g., ROM, floppy disks, hard disks, etc.), optical recording media (e.g., CD-ROMs, or DVDs), and other types of storage media.

The exemplary embodiments should be considered in a descriptive sense only and not for purposes of limitation. Descriptions of features or aspects within each exemplary embodiment should typically be considered as available for other similar features or aspects in other exemplary embodiments.

While the exemplary embodiments have been particularly shown and described with reference to certain exemplary embodiments thereof, it will be understood by those of ordinary skill in the art that various changes in form and details may be made therein without departing from the spirit and scope of the exemplary embodiments as defined by the following claims.

What is claimed is:

1. A medical image registration method comprising:
   performing a first registration by registering first medical images, including an image to be registered, obtained by imaging an object at a first time and an image to be displayed, obtained by imaging the object at a second time different from the first time;
   performing a second registration by registering a second medical image, having a different modality than a modality of the first medical images, with the image to be registered; and
   extracting a cross-section of one of the first medical images, corresponding to a cross-section of the second medical image, from the image to be displayed, according to the first registration and the second registration,
   wherein a first sub-object of the object is clearer than a second sub-object of the object in the image to be registered such that the second registration is performed using the first sub-object, and the second sub-object is clearer than the first sub-object in the image to be displayed.

2. The medical image registration method of claim 1, wherein the cross-section of one of the first medical image and the cross-section of the second medical image correspond to a same view of an object.

3. The medical image registration method of claim 1, wherein a sub-object included in the image to be registered has a different degree of clarity from a same sub-object included in the image to be displayed.

4. The medical image registration method of claim 1, further comprising calculating a first conversion relationship which is a conversion relationship between the image to be registered and the image to be displayed, via the first registration.

5. The medical image registration method of claim 1, further comprising calculating a second conversion relationship which is a conversion relationship between the second medical image and the image to be registered, via the second registration.

6. The medical image registration method of claim 1, wherein the extracting the cross-section of one of the first medical images comprises:
   converting coordinate information about the cross-section of the second medical image into coordinate information in the image to be registered according to the second registration;
   converting the coordinate information in the image to be registered into coordinate information in the image to be displayed according to the first registration; and
   extracting the cross-section of the one first medical image having the coordinate information in the image to be displayed, from the image to be displayed.

7. The medical image registration method of claim 1, further comprising displaying the cross-section of the one first medical image and the cross-section of the second medical image together.

8. The medical image registration method of claim 1, wherein
   the one first medical image is a pre-captured medical image, and
   the second medical image is captured in real time.

9. The medical image registration method of claim 1, wherein
   the first medical image is at least one of a magnetic resonance (MR) image, a computed tomography (CT) image, a position emission tomography (PET) image, a single-photon emission computed tomography (SPECT) image, and an X-ray image, and
   the second medical image is an ultrasound image.

10. A medical imaging apparatus comprising:
    an image processor configured to perform a first registration by registering first medical images, including an image to be registered, obtained by imaging an object at a first time and an image to be displayed, obtained by imaging the object at a second time different from the first time,
    perform a second registration by registering a second medical image, having a different modality than a modality of the first medical images, with the image to be registered
    and extract a cross-section of one of the first medical images, corresponding to a cross-section of the second medical image, from the image to be displayed, according to the first registration and the second registration; and
    a display configured to display the cross-section of the one first medical image and the cross-section of the second medical image together,
    wherein a first sub-object of the object is clearer than a second sub-object of the object in the image to be registered such that the second registration is performed using the first sub-object, and the second sub-object is clearer than the first sub-object in the image to be displayed.

11. The medical imaging apparatus of claim 10, wherein the cross-section of the one first medical image and the cross-section of the second medical image correspond to a same view of an object.

12. The medical imaging apparatus of claim 10, wherein a sub-object included in the image to be registered has a different degree of clarity from a same sub-object included in the image to be displayed.

13. The medical imaging apparatus of claim 10, wherein the image processor is configured to convert coordinate information about the cross-section of the first medical image into coordinate information in the image to be registered according to the second registration, convert the coordinate information in the image to be registered into coordinate information in the image to be displayed according to the first registration, and extract the cross-section of the second medical image having the coordinate information in the image to be displayed, from the image to be displayed.

14. The medical imaging apparatus of claim 10, wherein the one first medical image is a pre-captured medical image, and
the second medical image is captured in real time.

15. A non-transitory computer-readable recording medium having recorded thereon a computer program which, when executed by a computer, causes the computer to perform a medical image registration method of claim 1.

16. A medical imaging apparatus comprising:
an image processor configured to register an image to be registered of a first medical image, obtained by imaging an object at a first time with an image to be displayed of the first medical images, obtained by imaging the object at a second time different from the first time and determine a first conversion relationship between the registered image to be registered and the registered image to be displayed
and register the image to be registered with a second medical image different from the first medical image and determine a second conversion relationship between the registered image to be registered and the registered second medical image; and
a display configured to display a cross-section of the image to be displayed and a cross-section of the second medical image, which corresponds to the cross-section of the image to be displayed, according to the first conversion relationship and the second conversion relationship,
wherein a first sub-object of the object is clearer than a second sub-object of the object in the image to be registered such that the second registration is performed using the first sub-object, and the second sub-object is clearer than the first sub-object in the image to be displayed.

17. The medical imaging apparatus of claim 16, wherein the first medical image is a pre-stored image, and the second medical image is an image captured in real time.

18. The medical imaging apparatus of claim 16, wherein the first and second conversion relationships represent coordinate conversions based on a Digital Imaging and Communication in Medicine (DICOM) standard.

* * * * *